(12) United States Patent
Tornier

(10) Patent No.: US 6,802,864 B2
(45) Date of Patent: Oct. 12, 2004

(54) PATELLAR IMPLANT AND KNEE PROSTHESIS INCORPORATING SUCH AN IMPLANT

(75) Inventor: Alain Tornier, Saint Ismier (FR)

(73) Assignee: Toriner SA, Saint Ismier (FR)

( * ) Notice: Subject to any disclaimer, the term of this patent is extended or adjusted under 35 U.S.C. 154(b) by 0 days.

(21) Appl. No.: 10/281,976

(22) Filed: Oct. 29, 2002

(65) Prior Publication Data

US 2003/0083751 A1 May 1, 2003

(30) Foreign Application Priority Data

Oct. 30, 2001 (FR) .............................................. 01 14068

(51) Int. Cl.⁷ .................................................. A61F 2/38
(52) U.S. Cl. ................................................. 623/20.18
(58) Field of Search ........................ 623/20.18, 20.19, 623/20.2

(56) References Cited

U.S. PATENT DOCUMENTS 3,927,423 A * 12/1975 Swanson .................... 623/20.2
4,158,894 A * 6/1979 Worrell .................... 623/20.18
5,609,640 A    3/1997 Johnson
5,738,686 A    4/1998 Kubein-Meesenburg et al.
6,047,425 A    4/2000 Khazaal

FOREIGN PATENT DOCUMENTS

| EP | 0021421 | 5/1984 |
| FR | 2700260 | 7/1994 |
| WO | 9725006 | 7/1997 |

OTHER PUBLICATIONS

Search report EP 02 35 6214.

* cited by examiner

Primary Examiner—Corrine McDermott
Assistant Examiner—Thomas J Sweet
(74) Attorney, Agent, or Firm—Dowell & Dowell, P.C.

(57) ABSTRACT

A patellar implant for total or partial prosthesis of the knee joint incorporates an outer articular surface and an inner articular surface provided to cooperate respectively with an outer side and an inner side of a femoral trochlea or of a femoral prosthetic component. The inner and outer articular surfaces are separated by a transition ridge which is curved, as viewed from a front of the implant, so as to be concave facing the outer articular surface. The outer articular surface is concave in a plane parallel to a sagittal plane and in a transverse plane of the knee joint.

9 Claims, 3 Drawing Sheets

PATELLAR IMPLANT AND KNEE PROSTHESIS INCORPORATING SUCH AN IMPLANT

BACKGROUND OF THE INVENTION

Field of the Invention

The present invention relates to a patellar implant and to a total or partial knee prosthesis incorporating such an implant.

DESCRIPTION OF THE RELATED ART

In the domain of knee prostheses, it is known to fit a natural patella with an implant intended to form one or more articular surfaces provided to cooperate with the femoral articular surfaces, whether it be question of natural surfaces or, most often, of prosthetic surfaces.

It is known, for example from U.S. Pat. No. 5,609,640 or from EP-A-0 021 421, to produce a patellar implant in the shape of a spherical dome or mushroom. Taking into account its geometry, such an implant is in point or virtually point contact with each condyle, which induces considerable localized stresses in the implant, on the one hand, and in the femoral prosthetic component or the femur, on the other hand. It is also known from FR-A-2 700 260 to produce a patellar component with two articular surfaces, of spherical and concave shape, which are symmetrical with respect to the sagittal plane and separated by a joining surface likewise symmetrical with respect to this plane. Taking into account the geometry of the Joining surface, the articular surfaces can generally not be in surface abutment against the trochlea during a whole movement of flexion or of extension of the knee.

This imperfect congruence between the articular surfaces provided respectively on the patellar implant and on the femur also results in a medio-lateral instability of the patella, which may lead to an unnatural positioning of the patella. This lack of congruence also induces an instability of the patella when pivoting in the sagittal plane, this reducing the efficiency of the extensor muscle and tending to increase wear of the articular surfaces in contact. Taking these limitations into account, such an implant must be fitted very precisely, otherwise it cannot perform its function.

It is a particular object of the present invention to overcome these drawbacks by proposing a patellar implant whose geometry is adapted to allow an efficient bearing on the trochlea of the femur, such bearing remaining congruent in the different positions of the knee joint.

SUMMARY OF THE INVENTION

To that end, the present invention relates to an implant of the aforementioned type, which comprises an outer articular surface and an inner articular surface provided to cooperate respectively with an outer side and an inner side of a femoral trochlea or of a femoral prosthetic component and joined together by a transition ridge, while the outer articular surface is concave in a plane parallel to the sagittal plane of the joint and in a transverse plane. This implant is characterized in that the transition ridge is curved as viewed from the front of the implant, with a concavity facing the outer articular surface.

Within the framework of the present invention, the adjective "inner" corresponds to that side of a knee joint oriented towards the other knee, while the adjective "outer" corresponds to the side facing away from the other knee. The sagittal plane is a plane intersecting the knee from rear to front in a median zone, while a transverse plane is a plane perpendicular to the patellar tendons and to the tendons of the quadriceps.

Thanks to the invention, the congruence of the articular surfaces provided on the implant and the trochlea is widely improved with respect to the state of the art. In particular, the concavity of the outer articular surface in the two planes perpendicular with respect to each other makes it possible to increase the stability of the contact and to reduce the wear of this surface. This double concavity, possibly associated with the convexity of the inner articular surface, also makes it possible to adjust the patella by a pivoting about the outer side of the femur, with the result that the implant and the patella are permanently correctly positioned with respect to the condyles and to the trochlea, without loss of congruence. The curved nature of the ridge contributes to the definition of the outer articular surface and is compatible with the afore-mentioned movement of adjustment, this ridge being engaged in the trochlea. It is a deliberate object of the invention to promote the congruence of the outer articular surfaces respectively provided on the implant and at the level of the outer side of the trochlea or of the outer condyle, whether it be question of a natural condyle or of a prosthetic element, as the bearing efforts of the patella on the condyles essentially transit via these outer surfaces.

According to advantageous but non-obligatory aspects of the invention, the implant incorporates one or more of the following characteristics:

- The centre of curvature of the transition ridge is located outside or on the periphery of the implant, seen from front view. This corresponds to the fact that the radius of curvature of this ridge is relatively large.
- The outer articular surface of the implant is a surface of revolution.
- Seen from front view, the implant is substantially ovoidal in shape.
- The inner articular surface of the implant is planar or convex in a plane parallel to the sagittal plane. The fact that this surface is planar or convex in a plane parallel to the sagittal plane and that it offers less congruence is less favourable than the situation relative to the outer articular surface, which is not prohibitive as the efforts transiting via this surface are less than those transiting via the outer articular surface. Moreover, the planar or convex nature of this surface in such a plane allows this surface to slide on the inner condyle during a movement of adjustment of the implant, by pivoting of its outer articular surface on the outer condyle.
- Two lateral bevels extend in directions substantially perpendicular to the sagittal plane and join the respective ridges of the articular surfaces to a peripheral edge of the implant. These bevels avoid a possible blocking of the implant on a corner or an edge of a femoral prosthetic surface.
- The implant is composed of a one-piece plastics component which allows it to have a sufficient thickness, without risk of metal/metal contact between the femoral prosthetic element and a reinforcing plate such as exists in an implant made of two materials.

The invention also relates to a total or partial prothesis of the knee which comprises an implant as described hereinabove. Such a prosthesis is easier for the surgeon to implant, insofar as the implant may be positioned with a greater tolerance, the implant tending to adjust its position with respect to the condyle by the congruence of its outer articular surface and of the outer condyle. Such a prosthesis also tends to wear out less than the known prostheses.

BRIEF DESCRIPTION OF THE DRAWINGS

The invention will be more readily understood on reading the following description of two forms of embodiment of a patellar implant and of a prosthesis in accordance with its principle, given solely by way of example and made with reference to the accompanying drawings, in which.

DESCRIPTION OF PREFERRED EMBODIMENTS

Figure 1:
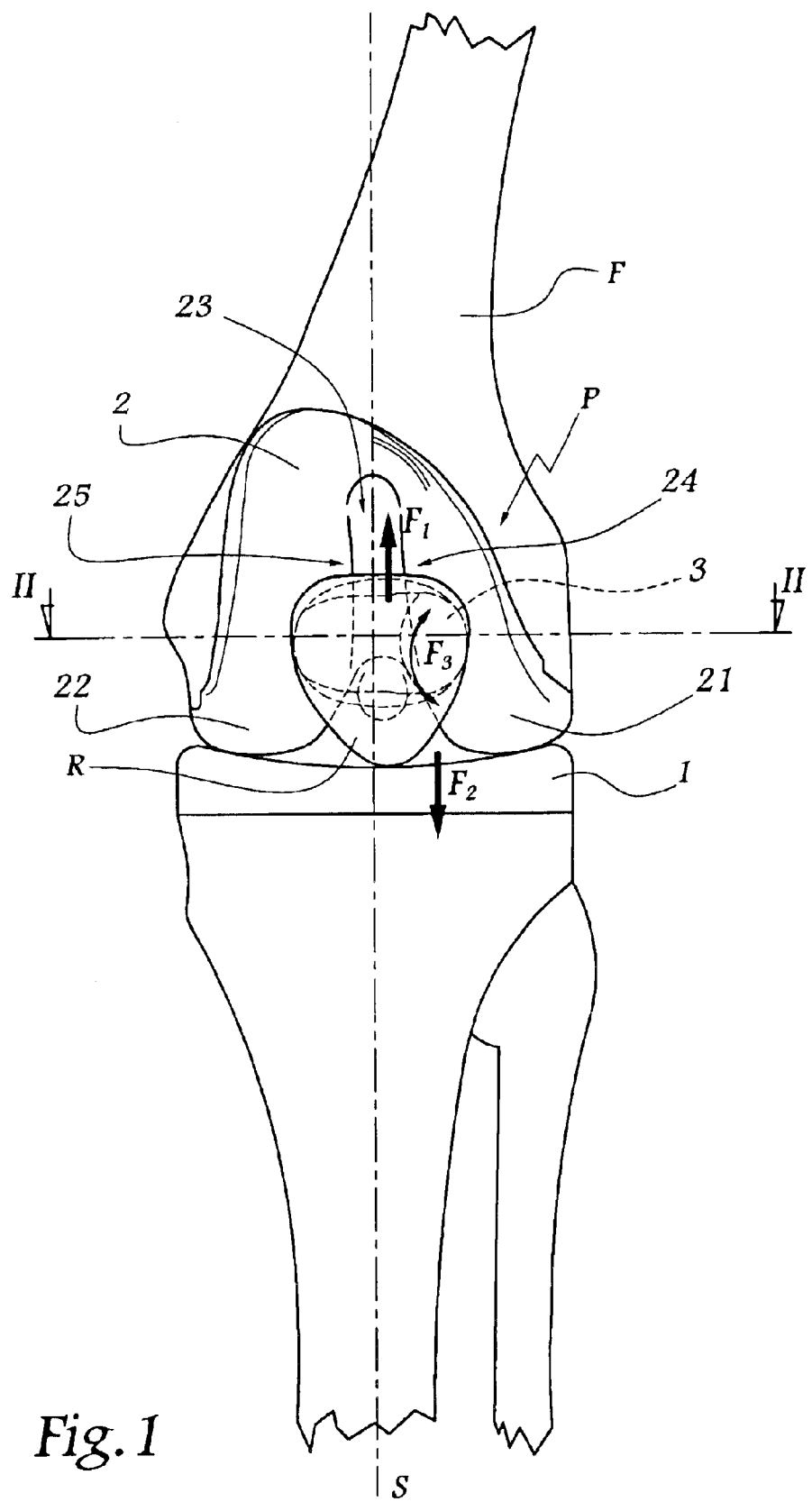
FIG. 1 is a front view of a knee joint fitted with a prosthesis according to the invention.

Referring now to the drawings, the prosthesis P shown in FIG. 1 comprises a tibial prosthetic component 1, a femoral prosthetic component 2 and a patellar implant 3 intended to be implanted in the patella R after resection thereof.

In the example shown, the knee in question is a left knee, thus its inner side is located on the left in FIG. 1 while its outer side is on the right.

The component 2 forms two condyles 21 and 22, respectively outer and inner, as well as two outer (24) and inner (25) sides of the femoral trochlea. These two condyles and these two sides are intended to receive the implant 3 in abutment.

The implant 3 is capable of movements of translation with respect to the trochlea 23 defined by the component 2, such movements being represented by arrows $F_1$ and $F_2$.

The implant 3 is also capable of movements of pivoting about the condyle 21, as represented by double arrow $F_3$.

The geometry of the implant 3 may be seen in FIGS. 2 to 7.

This implant comprises an outer articular surface 31 intended to come into abutment against the condyle 21 or the outer side 24 and an inner articular surface 32 intended to come into abutment against the condyle 22 or the inner side 25.

A transition ridge 33 joins the surfaces 31 and 32 this ridge is not sharp, in that it is rounded.

Figure 2:
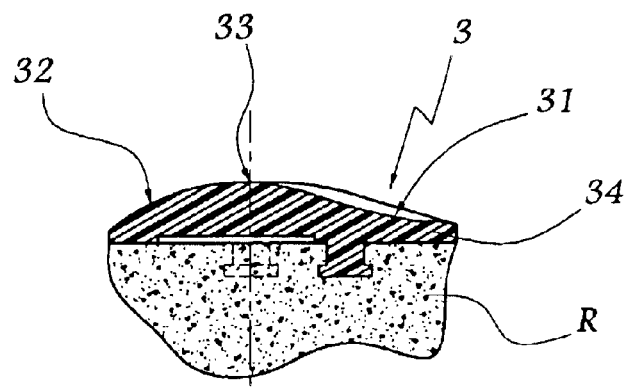
FIG. 2 is a section through the joint along line II—II of FIG. 1.
Figure 4:
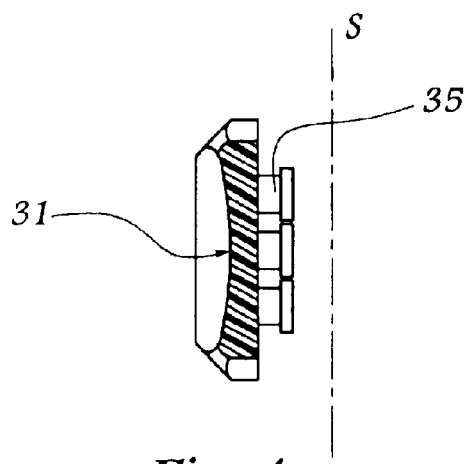
FIG. 4 is a section along line IV—IV of FIG. 3.

The surface 31 is concave in the plane of FIG. 4, i.e. in a plane parallel to the sagittal plane S of the, joint represented by its trace in FIGS. 1 and 2.

In the plane of FIG. 2, which is a transverse plane with respect to the joint, this surface 31 is also concave.

In this way, the surface 31 is bi-concave and may slide and pivot in the direction of arrow $F_3$ on the condyle 21 which is bi-convex.

Figure 5:
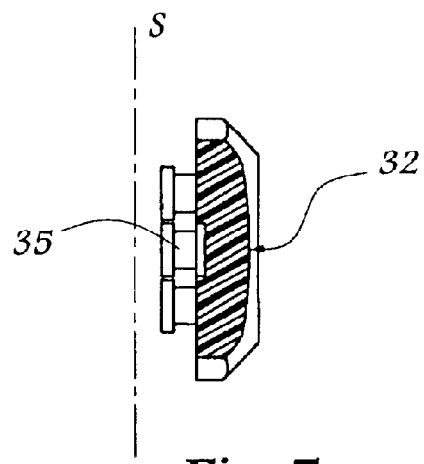
FIG. 5 is a section along line V—V of FIG. 3.
Figure 6:
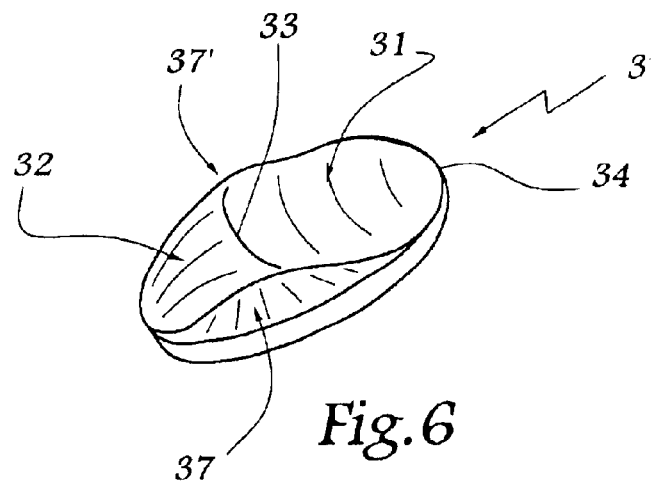
FIG. 6 is a view in perspective of the implant of FIGS. 3 to 5 seen from its front face.
Figure 7:
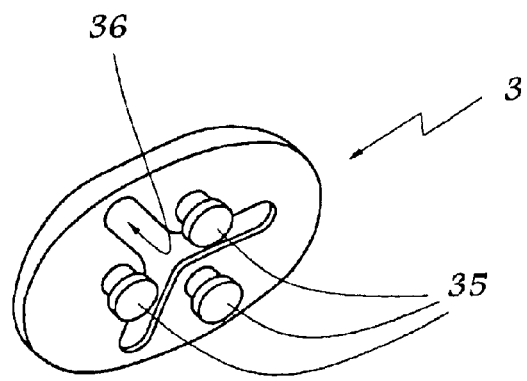
FIG. 7 is a view in perspective of the implant of FIGS. 3 to 6 seen from its rear face.

As for the surface 32, it is convex in the plane of FIG. 5, which is also parallel to the sagittal plane S, and convex in the plane of FIG. 2.

According to variant embodiments of the invention, the surface 32 might be planar in the plane of FIG. 5, and even concave in the plane of FIG. 2.

Figure 3:
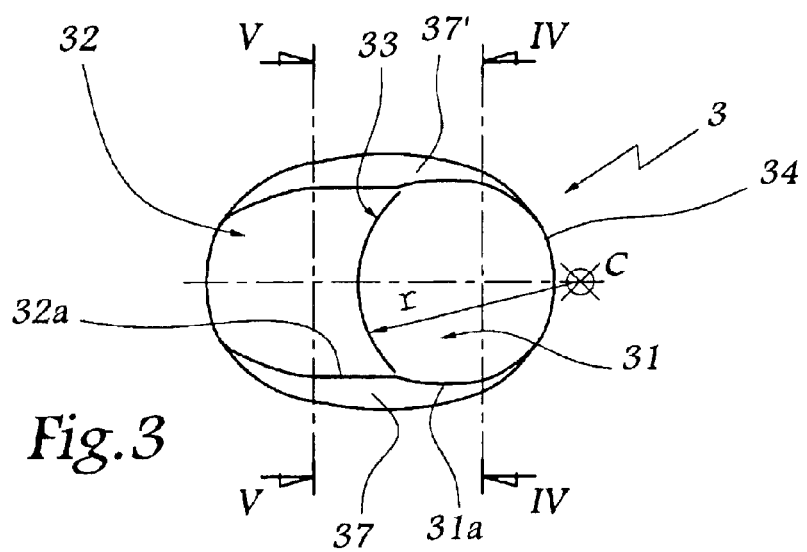
FIG. 3 is a front view of the patellar implant used in the prosthesis of FIGS. 1 and 2.

As is more particularly visible in FIG. 3, the ridge 33 is curved, with a concavity turned towards the surface 31.

"C" denotes the centre of curvature of the ridge 33. As is seen in FIG. 3, this centre of curvature lies outside the implant 3, towards the surface 31, so that the radius of curvature r of the ridge 33 is relatively large. In a variant, the centre "C" might be defined at a frontal peripheral ridge 34 of the implant 3.

Due to the geometry of the surfaces 31 and 32 and of the ridge 33, a surface bearing of the surfaces 31 and 21 on each other is obtained, while the bearing of the surfaces 32 and 22 on each other is linear or virtually point-like. This is justified by the fact that the efforts of compression of the patella R in the direction of the femur F transit essentially via the surfaces 31 and 21.

The geometry of the ridge 33 allows it to engage without difficulty in the trochlea 33 and to be compatible with displacements of the patella R with respect to the femur F represented by arrows $F_1$ to $F_3$.

The implant 3 is also provided with three studs 35 for anchoring in the patella R and with a substantially Y-shaped groove 36 which serves to promote anchoring of the implant 3 in a bed of cement.

In practice, the surface 31 is designed so that it constitutes a surface of revolution, in particular about an axis perpendicular to the plane of FIG. 3.

The implant 3 is also provided with two lateral bevels 37 and 37' which join the respective edges 31a and 32a of the surfaces 31 and 32 with the peripheral edge 34 of the implant. These bevels avoid the creation of projecting zones which, in certain configurations of use of the prosthesis P, would risk jamming against the components 1 or 2.

Figure 8:
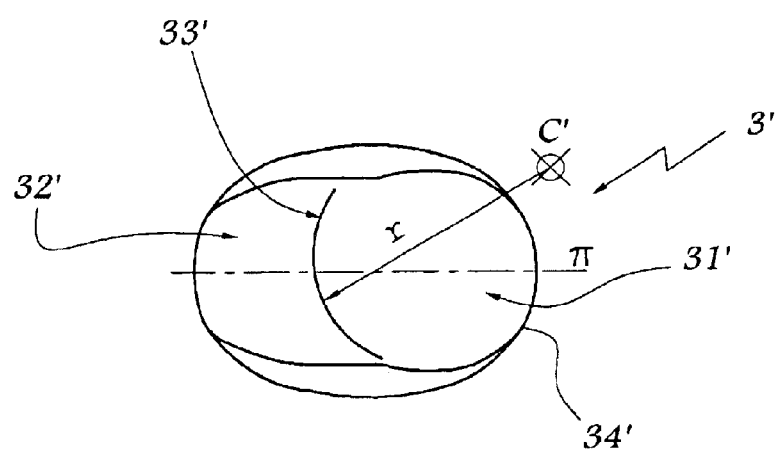
FIG. 8 is a view similar to FIG. 3 for an implant in accordance with a second form of embodiment of the invention.

In the second form of embodiment of the invention shown in FIG. 8, the implant 3' likewise comprises an outer articular surface 31', an inner articular surface 32' and a joining ridge 33'.

This embodiment differs from the preceding ones in that the centre of curvature C' of the ridge 33' does not lie in the median transverse plane π of the implant, which is the plane of section of FIG. 2 for the implant 3, but is offset with respect to this plane π, with the result that the ridge 33' is not symmetrical with respect to this plane π unlike the ridge 33 of the first embodiment. This variant makes it possible to accentuate or diminish the effect of pivoting in the direction of arrow $F_3$. Of course, the centre of curvature C' might be defined on the other side of the plane π in FIG. 8 and/or at the peripheral edge 34' of the implant 3', the radius of curvature r' of the ridge 33' being adapted accordingly.

What is claimed is:

1. A patellar implant for total or partial prosthesis of the knee joint, the implant including an outer articular surface and an inner articular surface provided to cooperate respectively with an outer side and an inner side of a femoral trochlea or of a femoral prosthetic component, said outer articular surface and said inner articular surface being separated by a transition ridge, said outer articular surface being concave in a plane parallel to a sagittal plane of the knee joint and in a transverse plane, and wherein said ridge is continuously concavely curved facing said outer articular surface, as viewed from a front of the implant.

2. The implant of claim 1, wherein said ridge defines a center of curvature located outside or on a peripheral edge of the implant.

3. The implant of one of claim 1, wherein said outer articular surface is a surface of revolution.

4. The implant of one of claim 1, wherein the implant, as viewed from the front, has a substantially ovoidal shape.

5. The implant of one of claim 1, wherein said inner articular surface is planar or convex in a plane parallel to the sagittal plane of the knee joint.

6. The implant of claim 1, including two lateral bevels extending in directions substantially perpendicular to the sagittal plane and joining respective edges of said outer and inner articular surfaces to a peripheral edge of the implant.

7. The implant of claim 1, wherein the implant is a one-piece plastic component.

8. Total or partial knee prosthesis, including a patellar implant having an outer articular surface and an inner articular surface provided to cooperate respectively with an outer side and an inner side of a femoral trochlea or of a femoral prosthetic component, said outer articular surface and said inner articular surface being separated by a transition ridge, said outer articular surface being concave in a plane parallel to a sagittal plane of the knee joint and in a transverse plane, and wherein said ridge is continuously concavely curved facing said outer articular surface, as viewed from a front of the implant.

9. The total or partial knee prosthesis of claim 8 wherein said ridge defines a center of curvature located outside or on the peripheral edge of the implant.

* * * * *

UNITED STATES PATENT AND TRADEMARK OFFICE
CERTIFICATE OF CORRECTION

PATENT NO. : 6,802,864 B2
DATED : October 12, 2004
INVENTOR(S) : Alain Tornier

It is certified that error appears in the above-identified patent and that said Letters Patent is hereby corrected as shown below:

Title page,
Item [73], Assignee, should read -- Tornier SA, Saint Ismiere (FR) --

Signed and Sealed this

Ninth Day of August, 2005

JON W. DUDAS
*Director of the United States Patent and Trademark Office*

UNITED STATES PATENT AND TRADEMARK OFFICE
CERTIFICATE OF CORRECTION

PATENT NO.     : 6,802,864 B2
DATED          : October 12, 2004
INVENTOR(S)    : Alain Tornier It is certified that error appears in the above-identified patent and that said Letters Patent is hereby corrected as shown below:

<u>Title page,</u>
Item [73], Assignee, should read -- Tornier SA, Saint Ismier (FR) --.

This certificate supersedes Certificate of Correction issued August 9, 2005.

Signed and Sealed this

Eleventh Day of October, 2005

JON W. DUDAS
*Director of the United States Patent and Trademark Office*